(12) United States Patent
Bechtel et al.

(10) Patent No.: US 11,672,448 B2
(45) Date of Patent: Jun. 13, 2023

(54) PROBE TIP FOR MEDICAL DEVICE

(71) Applicant: ViOptix, Inc., Newark, CA (US)

(72) Inventors: Kate LeeAnn Bechtel, Pleasant Hill, CA (US); Alex Michael Margiott, Andover, MA (US); Jennifer Elizabeth Keating, Campbell, CA (US); Kimberly Merritt Shultz, Mountain View, CA (US)

(73) Assignee: ViOptix, Inc., Newark, CA (US)

( * ) Notice: Subject to any disclaimer, the term of this patent is extended or adjusted under 35 U.S.C. 154(b) by 57 days.

(21) Appl. No.: 17/146,190

(22) Filed: Jan. 11, 2021

(65) Prior Publication Data

US 2021/0212615 A1 Jul. 15, 2021

Related U.S. Application Data

(60) Provisional application No. 62/959,787, filed on Jan. 10, 2020.

(51) Int. Cl.
*A61B 5/1455* (2006.01)

(52) U.S. Cl.
CPC ...... *A61B 5/14552* (2013.01); *A61B 2503/10* (2013.01); *A61B 2503/40* (2013.01);
(Continued)

(58) Field of Classification Search
CPC ............ A61B 5/14552; A61B 2503/10; A61B 2503/40; A61B 2560/0214;
(Continued)

(56) References Cited

U.S. PATENT DOCUMENTS

| 6,901,221 B1* | 5/2005 | Jiang ...................... G02B 6/428 |
| | | 385/24 |
| 2013/0324816 A1* | 12/2013 | Bechtel ................ A61B 5/1455 |
| | | 600/331 |

FOREIGN PATENT DOCUMENTS

| EP | 2151900 | 11/2008 |
| WO | WO2013/166461 | 11/2013 |
| WO | WO2014/026200 | 2/2014 |

OTHER PUBLICATIONS

Rothmaier, Markus et al., Photonic textiles for pulse oximetry, Optics Express, Aug. 18, 2008 (published Aug. 11, 2008), pp. 12973-12986, vol. 16, No. 17.

(Continued)

*Primary Examiner* — Eric F Winakur
*Assistant Examiner* — Abid A Mustansir
(74) *Attorney, Agent, or Firm* — Aka Chan LLP

(57) ABSTRACT

A probe tip of an oximeter device includes first and second printed circuit boards (PCBs) that are coupled to the ends of optical fibers that transmit light between the PCBs and into patient tissue that is to be measured by the oximeter device. The PCBs are oriented at an angle between zero and ninety degrees so that the fibers have a curved shape between the locations at which the fibers are coupled to the first and second PCBs. The angular orientation of the PCBs and curved shape of the fibers allows the fibers to have a longer length than if the fibers were straight and allows for light transmitted through the fibers to have a uniform distribution across a cross-section of the fibers as the light is emitted from the fibers into patient tissue. The uniform distribution of light transmitted into patient tissue allows for reliable oximetry measurements.

17 Claims, 18 Drawing Sheets

(52) U.S. Cl.
CPC ............... *A61B 2560/0214* (2013.01); *A61B 2560/0418* (2013.01); *A61B 2562/0219* (2013.01); *A61B 2562/0271* (2013.01); *A61B 2562/166* (2013.01); *A61B 2562/18* (2013.01)

(58) Field of Classification Search
CPC .... A61B 2560/0418; A61B 2562/0219; A61B 2562/0271; A61B 2562/166; A61B 2562/18; A61B 2560/0431; A61B 2562/0233; A61B 2562/12
See application file for complete search history.

(56) References Cited

OTHER PUBLICATIONS

International Search Report, PCT Application PCT/US2021/013000, dated Apr. 19, 2021, 10 pages.

\* cited by examiner

PROBE TIP FOR MEDICAL DEVICE

CROSS-REFERENCE TO RELATED APPLICATIONS

This application claims the benefit of U.S. patent application 62/959,787, filed Jan. 10, 2020. This application is incorporated by reference along with all other references cited in these applications.

BACKGROUND OF THE INVENTION

The present invention relates generally to optical systems that monitor parameters related to oxygen levels in tissue. More specifically, the present invention relates to optical probes, such as compact, handheld oximeters, and sheaths for the optical probes that shield the optical probes from contaminants during use and communicate status information to the optical probes regarding contaminant protection so that the optical probes are reusable.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are the dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for an improved tissue oximetry devices and methods of shielding oximetry devices during use for reuse of the devices.

BRIEF SUMMARY OF THE INVENTION

Embodiments relate to compact, handheld oximeters and sheaths that house and shield the handheld oximeters from patient contact and contaminants during use and shield patients from contaminants on the handheld oximeters. Because a handheld oximeter is located in a sheath and cannot contaminate patient tissue, the handheld oximeter can be reused.

In an implementation, an oximeter device includes a housing; a processor, housed in the housing; a memory, housed in the housing, wherein the memory is coupled to the processor; a display, housed by the housing at a proximal end of the housing and visible from an exterior of the housing at the proximal end of the housing, wherein the display is coupled to the processor.

The oximeter device includes a probe tip, housed by housing at a distal end of the housing and visible from the exterior of the housing at the distal end of the housing, wherein the probe tip is coupled to the processor.

The probe tip includes a first printed circuit board (PCB), a second PCB, and a first optical fiber coupled to the first and second PCBs. The first PCB is positioned closer to the proximal end of the housing than the second PCB. The second PCB is positioned closer to the distal end of the housing than the first PCB.

A first surface of the first PCB faces the distal end of the housing, a second surface of the second PCB faces the proximal end of the housing, an angle between the first and second surfaces is nonzero and is less than ninety degrees (e.g., from about 65 degrees to about 70 degrees). A first end portion of the first optical fiber located at the first PCB is approximately transverse to the first surface of the first PCB. A second end portion of the first optical fiber located at the second PCB is approximately transverse to the second surface of the second PCB. A portion of the first optical fiber between the first and second end portions of the first optical fiber is curved.

The angular orientation of the PCBs and the curved shape of the fibers facilitated by the angular orientation of the PCBs allows the fibers to have a longer length than if the fibers were straight between parallel PCBs. This allows for light transmitted through the fibers to have a uniform distribution across a cross-section of the fibers as the light is emitted from the fibers into patient tissue. The uniform distribution of light transmitted into patient tissue allows for reliable oximetry measurements.

The handheld oximeters implementations are entirely self-contained, without any need to connect, via wires or wirelessly, to a separate system unit for making oximetry measurements. The sources and detectors of the oximetry device are arranged in an arrangement having various source-detector pair distances that allow for robust calibration, self-correction, and spatially-resolved spectroscopy in a compact probe. Other source-detector arrangements are also possible.

In an implementation, the handheld oximeter is a tissue oximeter that can measure oxygen saturation without requiring a pulse or heartbeat. A tissue oximeter of the invention is applicable to many areas of medicine and surgery, including plastic surgery. The tissue oximeter can make oxygen saturation measurements of tissue where there is no pulse; such tissue, for example, may have been separated from the body (e.g., a flap) and will be transplanted to another place in the body. The tissue oximeter can also make oxygen saturation measurements of tissue where there is a weak pulse, such as where perfusion is relatively low.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
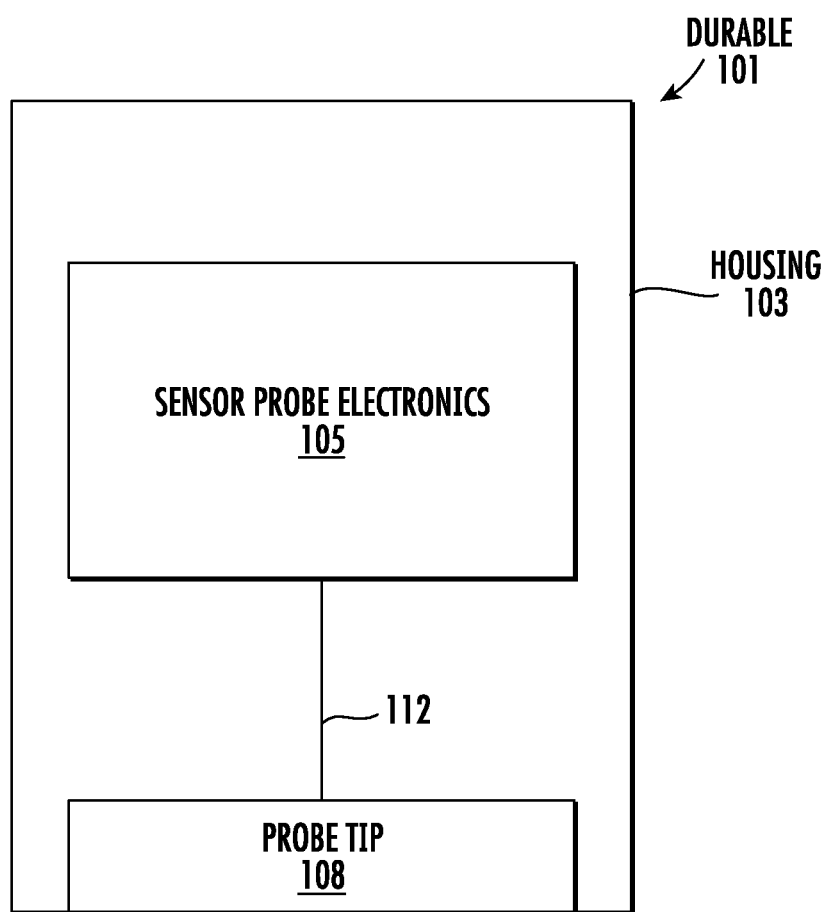
FIG. 1 shows a block diagram of a system unit for measuring various oximetry parameters of patient tissue.

Spectroscopy has been used for noninvasive measurements of various physiological properties in animal and human subjects. Visible (e.g., red light, green light, or both) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficients and the reduced scattering coefficients of the physiological medium by use of the photon diffusion approximation, Monte Carlo models, or other techniques. From the absorption coefficients at multiple wavelengths, concentrations of oxygenated and deoxygenated hemoglobins can be determined and from these concentrations, the tissue oxygen saturation can be calculated.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes of the index of refraction of the tissue and includes Mie scattering from larger structures such as mitochondria (the majority of tissue scattering is a result of mitochondria) and Rayleigh scattering from smaller structures such as intracellular vesicles. Absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations, and therefore, oxygen saturation within the volume of the tissue probed. Further, the wavelengths of the light source or light sources and the relative positions of the light source(s) with respect to a single detector or multiple ones of the detectors, allow tissue oximetry measurements to be made for a predetermined tissue depth. In an embodiment, one or more of the light sources and one or more of the detector source may emit and detect light so that oximetry measurements may be made for one or more predetermined tissue depths.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions.

Oximetry probes adapted for SRS and other spectroscopies can come into contact with tissue, other surfaces, fluids (both liquid and gas), or other elements that can contaminate the probes. An oximetry probe that contacts tissue, for example, can be contaminated by the tissue, bacteria on the tissue, viruses on the tissue, tissue fluid, debris on the tissue, the environment near the tissue, any one of these substances, other substances, or any combination of these substances. A sheath can shield an oximetry probe from contaminants, but the efficacy of a sheath can be compromised in a number of ways. The ways in which a sheath can be compromised, allowing an oximetry probe to be contaminated, can be known and unknown. For example, a sheath housing an oximetry device may open and allows contaminants to contact the oximetry probe. The sheath opening may be relatively small and not detectable by visual inspection and the small opening may allow contaminants to enter the sheath and contact the oximetry probe. The efficacy of a sheath can be compromised if the sheath has been previously used and the previous use is unknown. The efficacy of a sheath can also be compromised if the sheath is provided from an unknown source and the sterility or sanitation of the sheath is unknown. Either inside or outside surfaces of the sheath, or both, can be contaminated if the sheath is provided by an unknown source. If the previous use of a sheath is unknown and the sheath is reused, contaminants on the sheath from an initial use can be spread during subsequent use of the sheath. Sheaths and the oximetry probes in the sheath may be contaminated in a variety of other ways. Reuse of an oximetry probe after contamination may be precluded or may increase the cost of reuse due to the cost of sanitizing or sterilizing the oximetry probe. Oximetry probes and sheaths of the present invention are directed toward improved sanitation, sterilization, or both.

FIG. 1 shows a system unit 101 for measuring various parameters of tissue in a patient. System unit 101 is sometimes referred to as a durable system unit because the unit is reusable, such as when the unit is used in combination with a protective sheath. The parameters of the tissue measured by the system unit may include an oxygen saturation level (relative oxygen saturation, absolute oxygen saturation, or both), a total hemoglobin concentration, an oxygenated hemoglobin concentration, an deoxygenated hemoglobin concentration, blood flow, pulse rate, a signal level of light reflected from the tissue, melanin concentration of tissue, other tissue parameters, or any combination of the parameters. The system unit includes housing 103, sensor probe electronics 105, and a probe tip 108, which is connected to the sensor probe electronics via a wired connection 112. Connection 112 may be an electrical connection, an optical connection, or another wired connection including any number of wires (e.g., one, two, three, four, five, six, or more wires or optical fibers), or any combination of these or other types of connections. In other implementations, connection 112 may be a wireless connection, such as via a radio frequency (RF) or infrared (IR) connection.

Typically, the system unit is used by placing the probe tip in contact or close proximity to tissue (e.g., skin or internal organ or other tissue) at a site where tissue parameter measurements are desired. The system unit causes an input signal to be emitted by the probe tip into the tissue (e.g., human tissue). There may be multiple input signals, and these signals may have varying or different wavelengths of electromagnetic radiation. The input signal is transmitted into the tissue and reflected from the tissue or transmitted through the tissue.

Then, after transmission through the tissue or reflection from the tissue, the signal is received at the probe tip. This received signal is received and analyzed by the sensor probe electronics. Based on the received signal, the sensor probe electronics determine various parameters of the tissue, such as an oxygen saturation level, a total hemoglobin concentration, an oxygenated hemoglobin concentration, a deoxygenated hemoglobin concentration, a blood flow, a pulse, a signal level of light reflected from the tissue, melanin concentration of tissue, or other tissue parameters. One or any combination of these parameters can be displayed on a display screen of the system unit.

In an implementation, the system unit is a tissue oximeter, which can measure oxygen saturation and hemoglobin concentration, without requiring a pulse or heartbeat. A tissue oximeter of the invention is applicable to many areas of medicine, surgery (including plastic surgery and spinal surgery), post-surgery, athlete monitoring, and other uses. The tissue oximeter can make oxygen saturation and hemoglobin concentration measurements of tissue where there is no pulse, such as tissue that has been separated from the body (e.g., a tissue flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. There are various implementations of systems and techniques for measuring oxygen saturation, such as discussed in U.S. patent applications 62/959,757, 62/959,764, 62/959,778, 62/959,795, and 62/959,808, filed Jan. 10, 2020; Ser. Nos. 17/146,176, 17/146,182, 17/146,186, 17/146,194, 17/146,197, and 17/146,201, filed Jan. 11, 2021; and Ser. Nos. 29/720,112, 29/720,115, 29/720,120, and 29/720,122, filed Jan. 9, 2020. These patent applications are incorporated by reference along with all other references cited in these applications.

Figure 2:
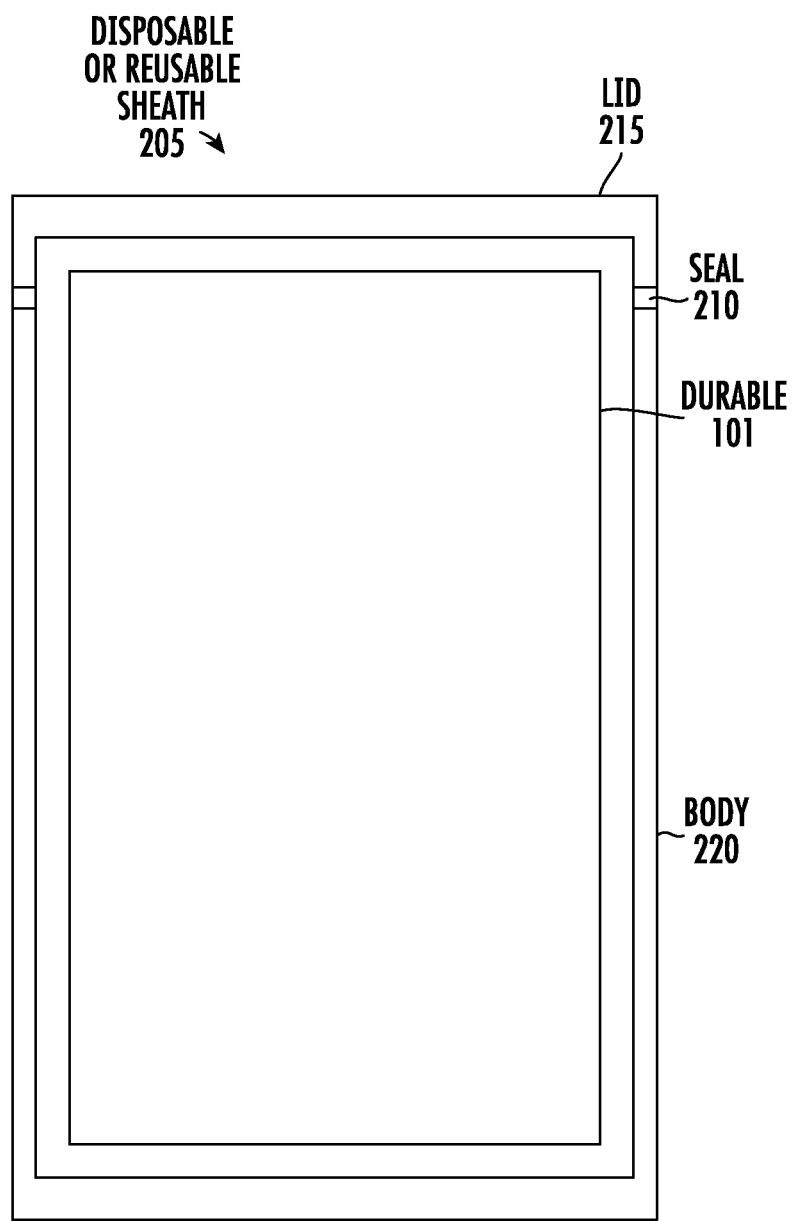
FIG. 2 shows a block diagram of the system unit housed in a sheath.

FIG. 2 shows system unit 101 housed in a sheath 205. The sheath includes a lid 215 and a body 220, which may be sealed to the lid via a seal 210. The lib may be separable from the body or may be connected to the body, such as via a hinge. The hinge may allow the lid to rotate to seal the lid to the body. The sheath may be a disposable sheath or a sheath that is reusable. For example, the system unit and sheath may travel with a patient from surgery (e.g., use) to post-surgery (e.g., reuse) for tissue monitoring.

With the lid opened, the system unit may be inserted into the sheath, and thereafter the lid may be sealed to the body to house and seal the system unit in the sheath. The system unit may then be used to make tissue parameter measurements in the sealed environment provided by the sheath. The sheath can protect the system unit from contacting elements that the sheath contacts, such as tissue, tissue fluid, biological agents (e.g., bacteria, viruses, and prions), debris, and other contaminants. When the lid is open and the seal is broken, the system unit may be removed from the sheath. Because the system unit is sealed into the sheath by the body, lid, and seal, the system unit can remain relatively clean, sanitized, or sterile for reuse.

Figure 3:
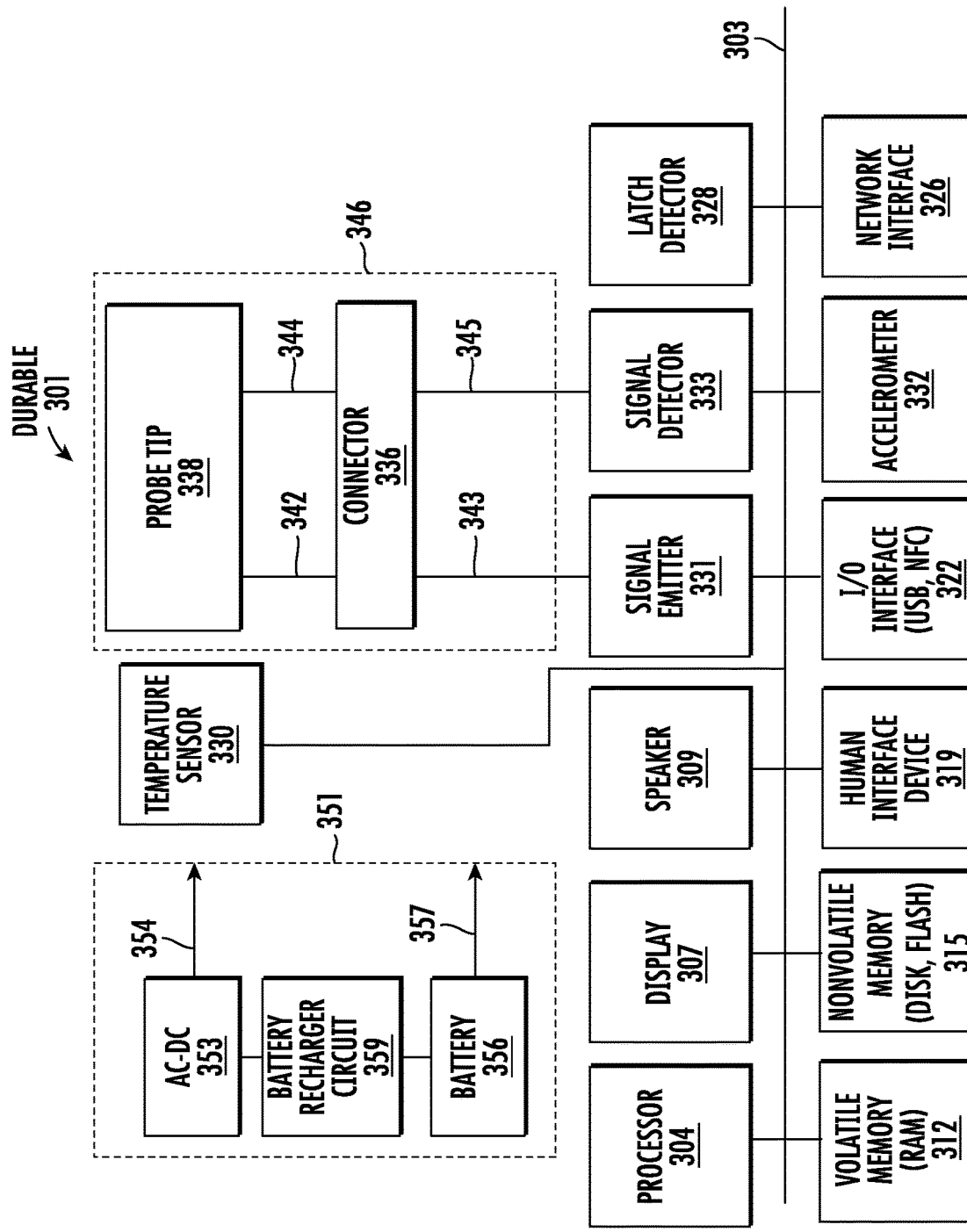
FIG. 3 shows a block diagram of the system unit, in an implementation.

FIG. 3 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, and accelerometer 332. These components are housed within housing 103. Different implementations of the system may include any number of the components described, in any combination or configuration, and may also include other components not shown.

The components are linked together via a bus 303, which represents the system bus architecture of the system unit. Although FIG. 3 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or other port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., a fiber optic cable), a number of waveguides (e.g., a number of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, or both. In this implementation, the signal emitters and signal detectors may be electrical emitters and detectors that control light emitters, light detectors, or both in the probe tip.

In an implementation, where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, signal emitter 331 includes one or more light sources that emit light at one or more specific wavelengths. In a specific implementation, the light sources emit four or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs).

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a power-down signal and may power down the system unit.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

In an implementation, the latch detector 328 is adapted to detect whether a latch of the sheath is latched or unlatched. If the latch is latched, then the system unit is housed and enclosed in the sheath. In this configuration, with the system unit housed and enclosed in the sheath, the system unit may not be contaminated by material contacting the outside surface of the sheath. If the latch is unlatched and the system unit is in the sheath, then the system unit might be contaminated with material contacting the outside surface of the sheath. That is, the seal that seals the lid of the sheath to the body of the sheath may be unsealed (i.e., opened) and contaminates may pass from outside of the sheath to the inside of the sheath where the system unit is located.

In an implementation, at least a first portion of the latch is metal. Other portions of the latch may be metal or other material, such as a plastic material. The first portion of the latch is a first distance from the latch detector when the latch is latched and is a second distance from the latch detector when the latch is unlatched. The first distance is less than the second distance.

In an implementation, the latch detector includes an inductor that can inductively couple to the first portion of the latch. The inductor can be driven with a direct current or an alternating current and thus detect when the first portion of the latch moves toward the latch detector or away from the latch detector. The latch detector can be calibrated so that the latch detector can detect when the latch moves to the first distance away from the latch detector or farther than the first distance away from the latch detector. The latch detector can include an analog-to-digital converter, a digital signal processor (DSP), or both that digitize and analyze the current flowing through the inductor. One or both of these circuits can communicate the digitalized information to the processor that can determine whether the latch is open or closed. The processor can display a message on the display to indicate whether the latch is open or closed, whether the seal for the sheath is sealed or unsealed, warn of potential contamination, or other messages associated with the latch being opened or closed.

In an embodiment, the latch detector is a capacitive detector that can capacitively couple to the latch. The capacitive detector can detect the latch in the latched position at a first distance from the capacitive detector and moving away from the latched position and the first distance.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C #, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses the system unit of the invention through a network such as the Internet. The user will be able to see the data being gathered by the system unit. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
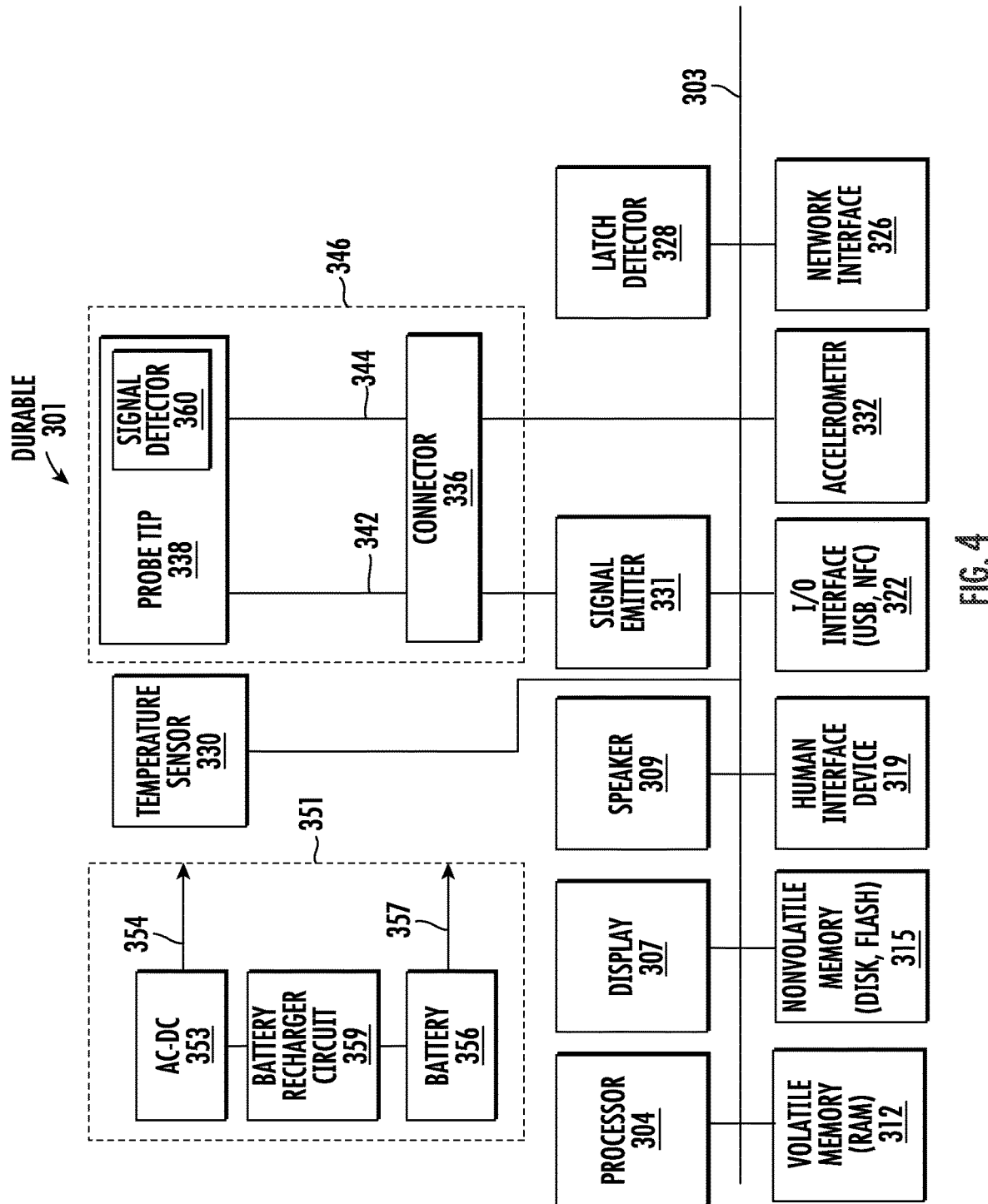
FIG. 4 shows a block diagram of the system unit, in an implementation.

FIG. 4 shows a block diagram of system unit 401, in an implementation. System unit 401 is similar to system unit 301 but differs in that the signal detector 344 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 5:
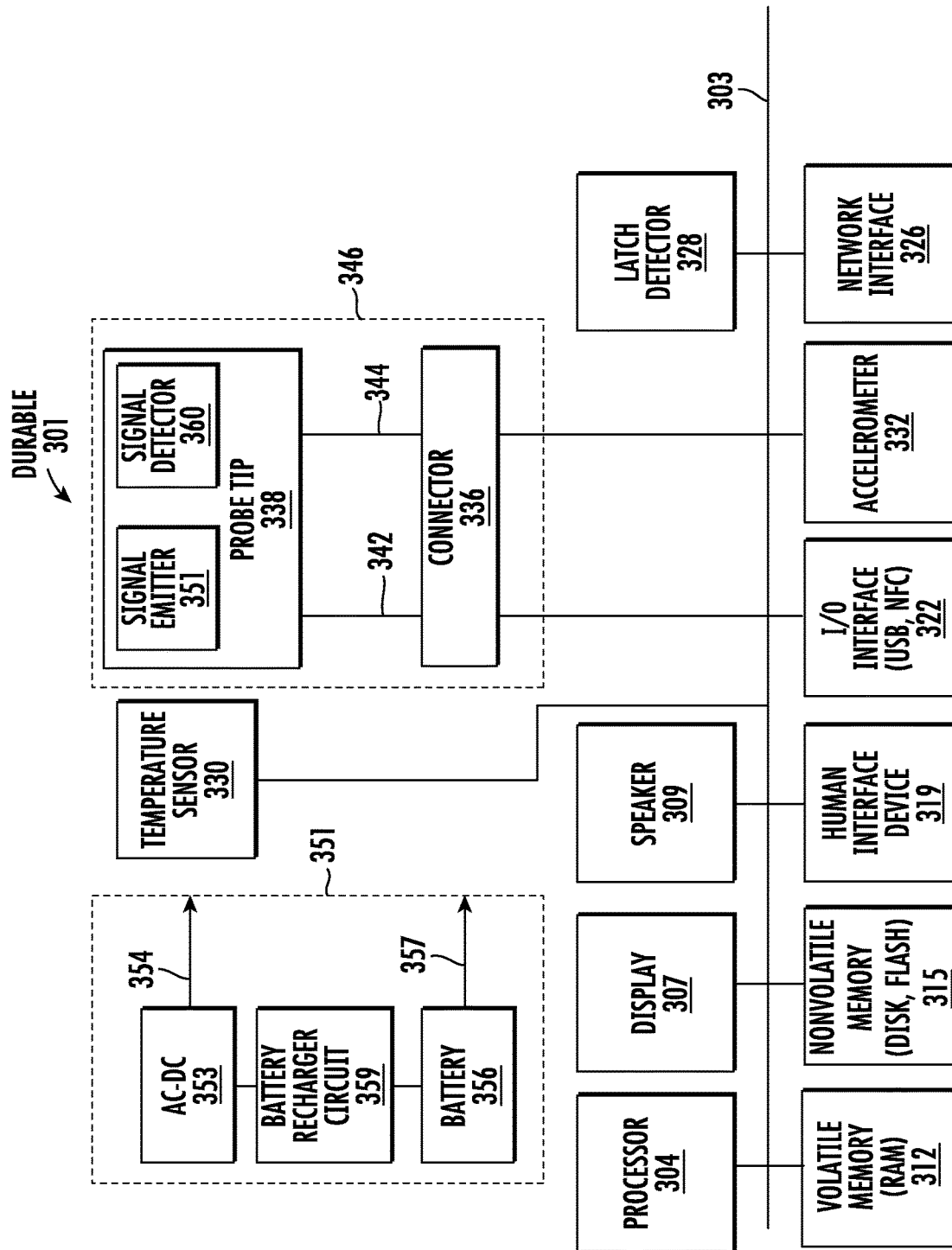
FIG. 5 shows a block diagram of the system unit, in an implementation.

FIG. 5 shows a block diagram of system unit 501, in an implementation. System unit 501 is similar to system units 301 and 401 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector.

Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system is battery operated. The DC output of a battery 356 is connected (indicated by an arrow 357) to the components of the system unit needing power. The battery may be recharged via a recharger circuit 359, which received DC power from the AC-to-DC converter. The AC-to-DC converter and recharger circuit may be combined into a single circuit.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 6:
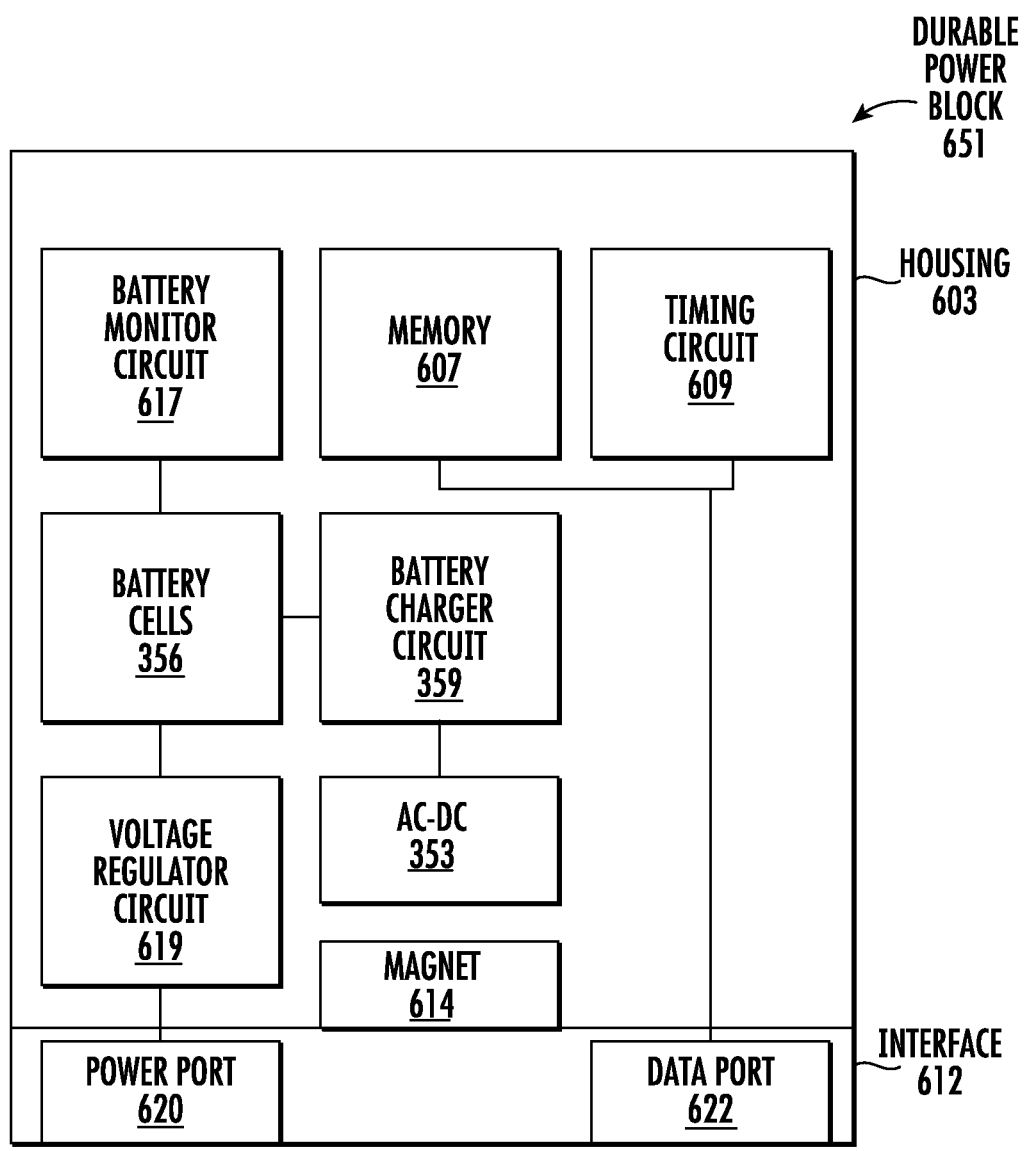
FIG. 6 shows a diagram of the power block of the system unit, in an implementation.

FIG. 6 shows block 651 that is a power block, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage. In an implementation, if the identifier is not a known identifier that is known to the system unit, then the processor with not allow the system unit to operate with the power block. That is, the system unit will not operate with a power block manufactured by an unknown manufacturer. Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements without displaying information on the display about the authenticity or the inauthenticity of the power block.

In an implementation, the memory of the power block stores an indicator that indicates whether the battery has been previously used. The indicator may be the time information for the amount of time that the power block has operated. A nonzero use time stored in the memory is an indicator that the power block has been previously used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that retrieved the system unit from the power block's memory, then the system unit will not operate with the power block. The implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts. The electrical contacts are arranged in an arrangement, such as in a row, in a square, in a rectangle, another arrangement. The system unit includes a power port that includes at least two electrical contacts (e.g., a power contact and a ground contact) and includes a data port that includes at least two electrical contacts. The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

Figure 7:
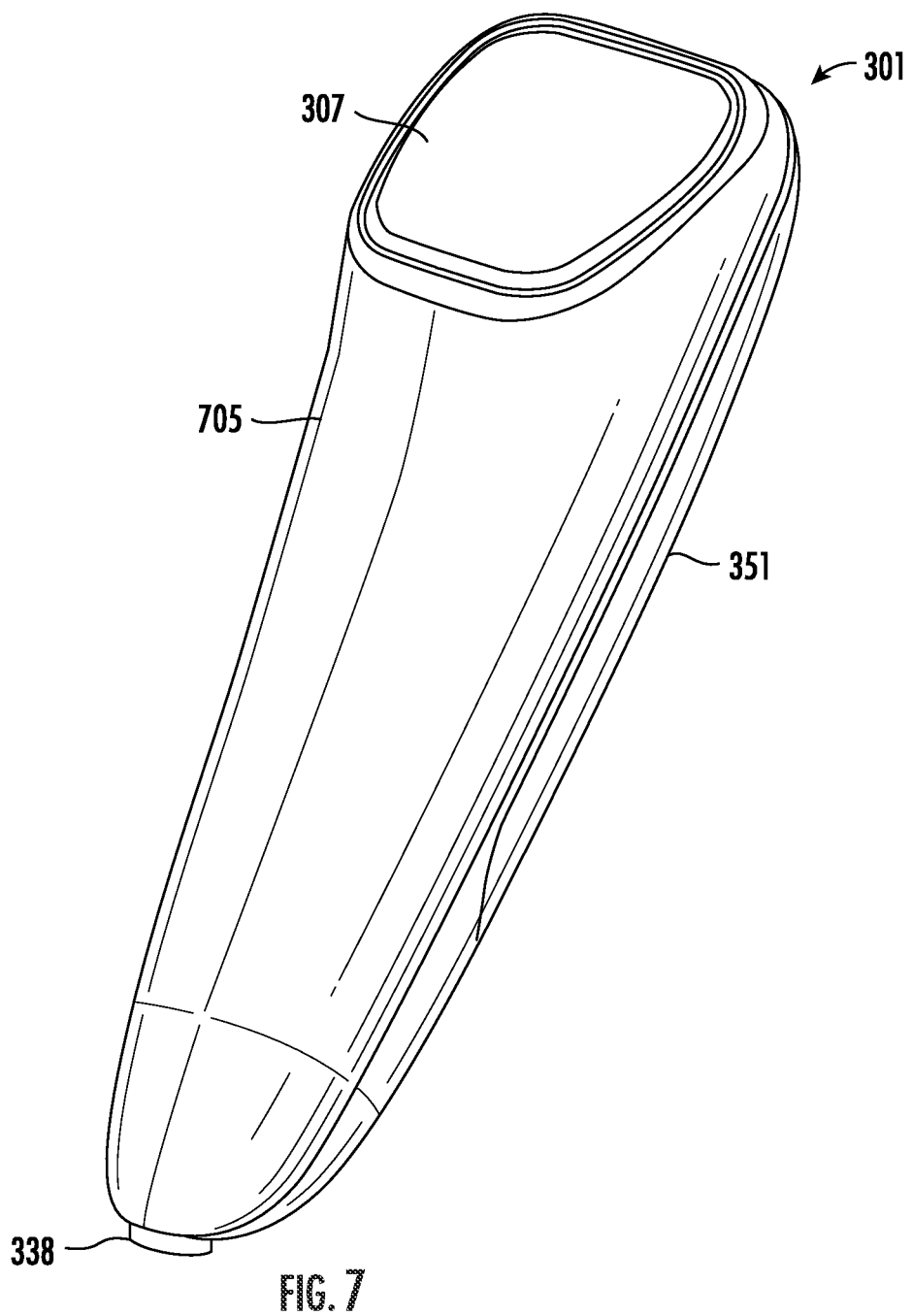
FIG. 7 shows a perspective view of the system unit and the power block.

FIG. 7 shows a perspective view of the system unit 301 and power block 351 coupled to the system unit, in an implementation. The display 307 of the system unit is located at a first end of the system unit and the probe tip 338 is located at a second end of the system unit where the first and second ends of proximal and distal ends of the unit. The housing of the system unit tapers from the first end to the second end. The described circuit elements are housed in the housing 705 of the system unit. When the probe face of the system unit is in contact with tissue, the display faces away from the tissue for easy visibility of the display.

Figure 8:
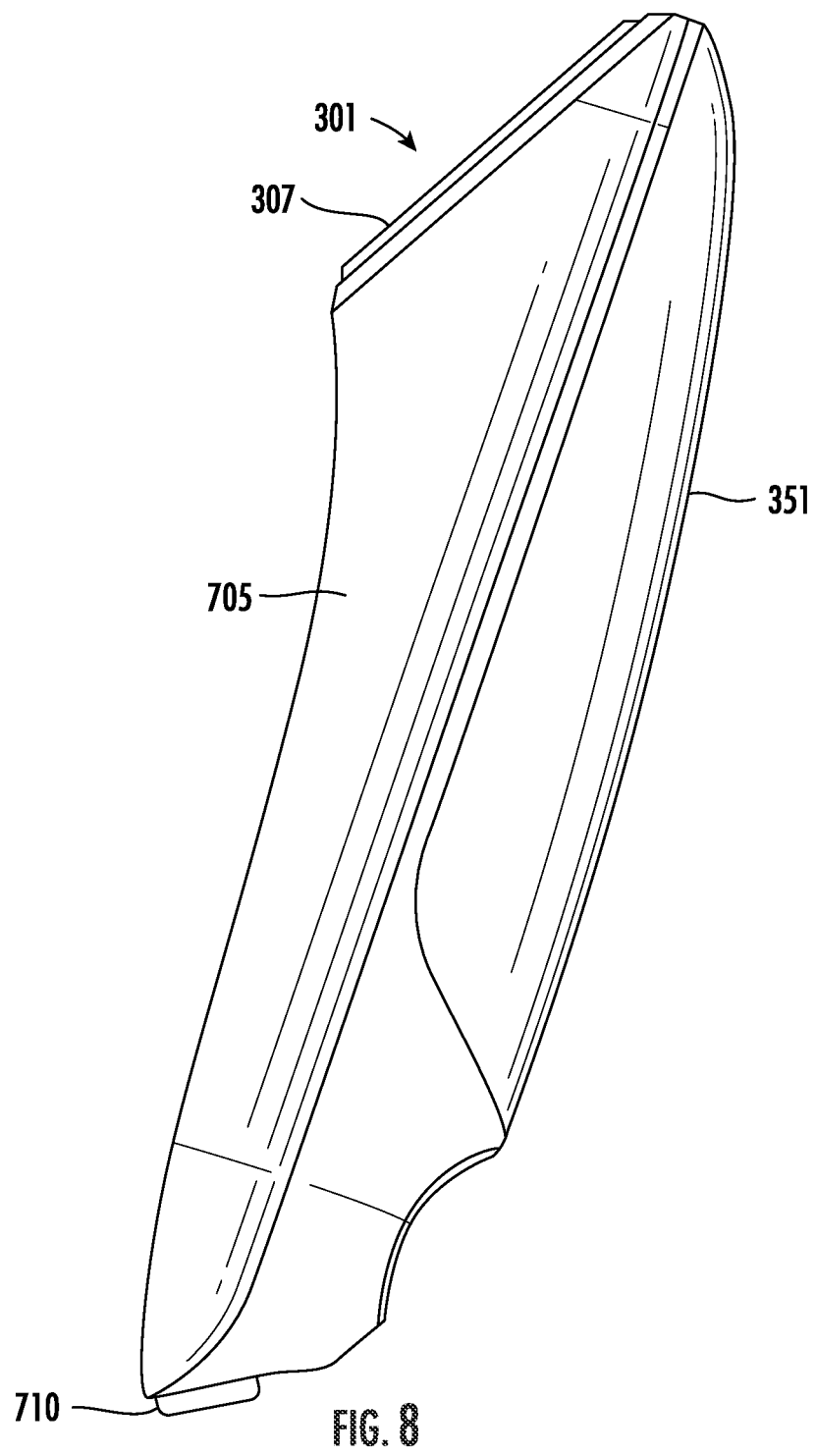
FIG. 8 shows a side view of the system unit.

FIG. 8 shows a side view system unit 301, in an implementation. The housing 705 of the system unit includes a bezel 710 that houses a portion of the probe tip. The bezel includes an opening the exposes a probe face of the probe tip.

Figure 9:
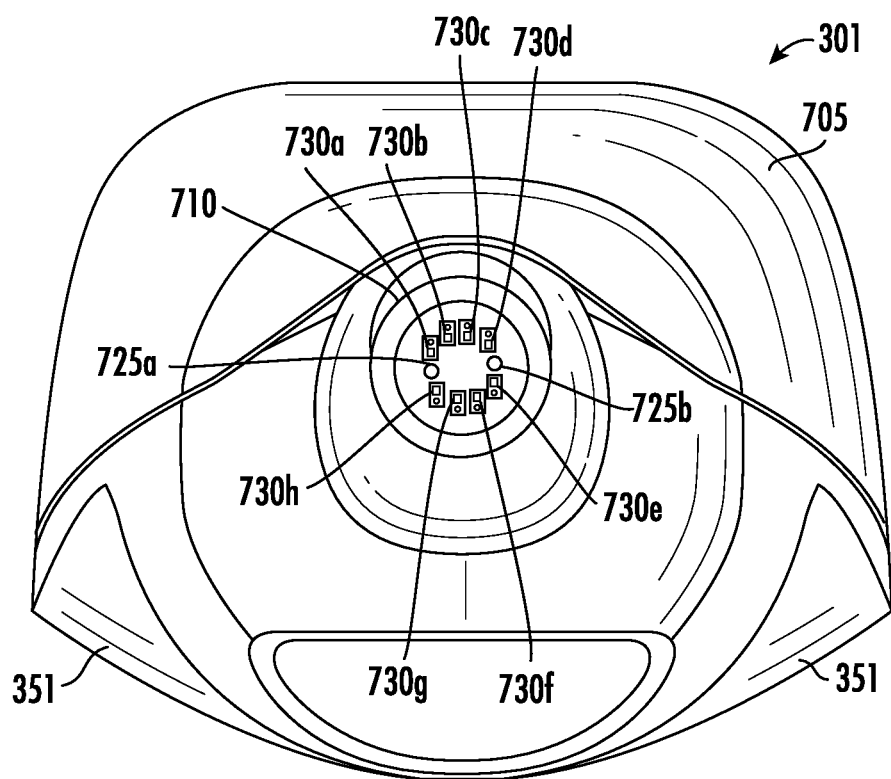
FIG. 9 shows an end view of the system unit.

FIG. 9 shows an end view of the second end of the system unit, in an implementation. The end of bezel 710 is shown with the probe face 715 in the opening of the bezel. The probe face may include an aperture plate 720 that includes a number of source apertures, for example, source apertures 725a and 725b, and includes a number of detector apertures 730a-730h. Each of the source apertures may be included in a source structure that may include light sources, such as one or more of optical fibers, laser diodes, LEDs, one or more portions of the aperture plate, or other structures at the probe tip in any combination. Each of the detector apertures may be included in a detector structure that may include light detectors, such as one or more of optical fibers, photodetectors, one or more portions of the aperture plate, or other structures at the probe tip in any combination.

Figure 10:
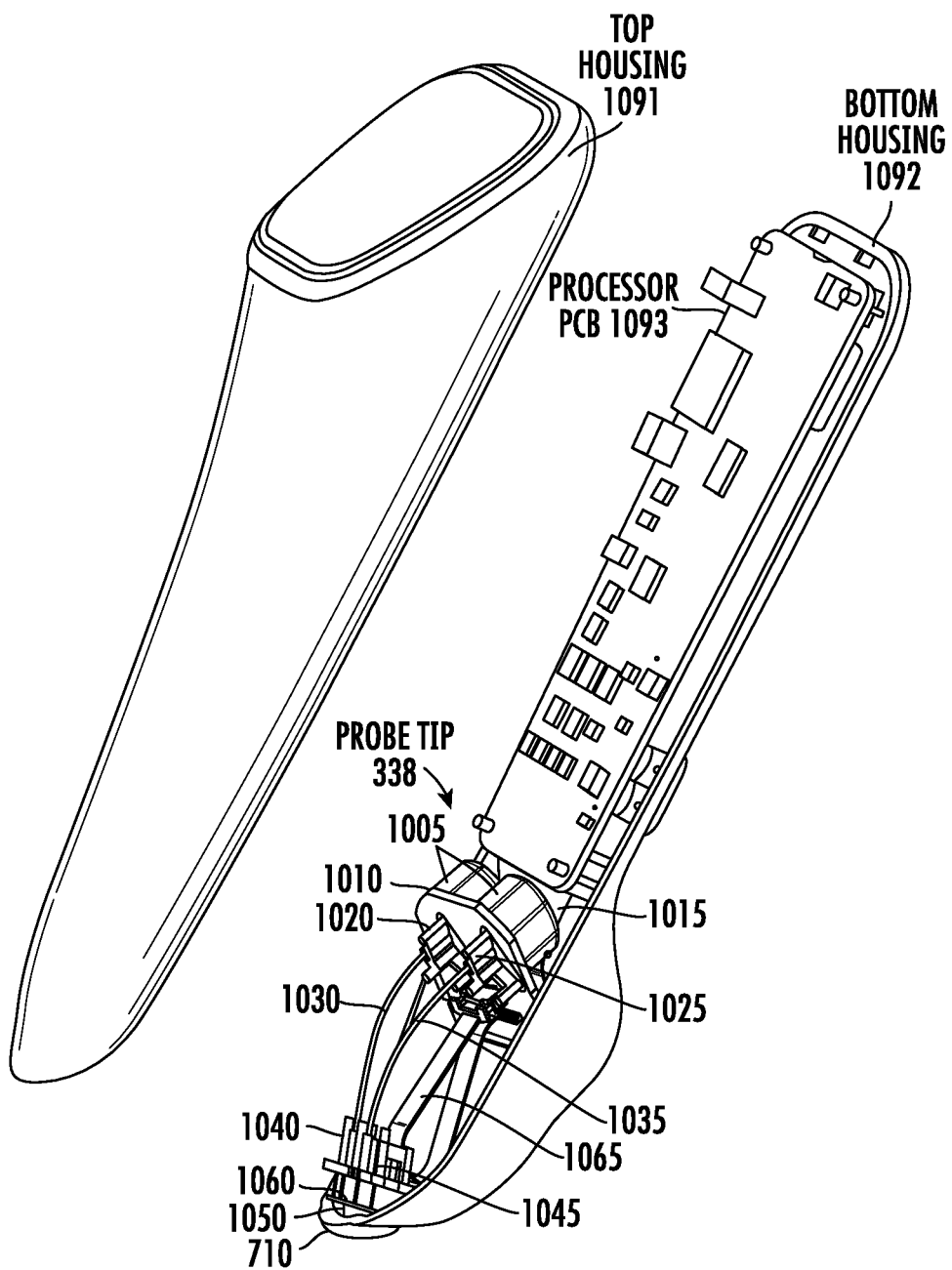
FIG. 10 is a perspective view of a probe head, in an implementation.

FIG. 10 shows a view of the system unit with a top housing 1091 of the system unit separated from a bottom housing 1092 of the system unit. This figure shows a PCB 1093 on which various circuits of the system unit are mounted, such as the processor 304, volatile memory 312, nonvolatile memory 315, human interface device (HID) 319, input-output (I/O) interface 322, network interface 326, and accelerometer 332.

The probe tip 338 is attached to a lower portion of the bottom housing. The probe tip may be connected to the bottom housing by mechanical fasteners, an adhesive (e.g., an glue, such as epoxy glue), another device, or any combination of these features. The probe tip includes two reflector domes 1005, an LED PCB 1010, a first optical fiber holder 1020, a second optical fiber holder 1025, a third optical fiber holder 1040, a fourth optical fiber holder 1045, a first optical fiber 1030, a second optical fiber 1035, a first PCB 1050, a second PCB 1060, a first ribbon cable 1015, and a second ribbon cable 1065.

Figure 11:
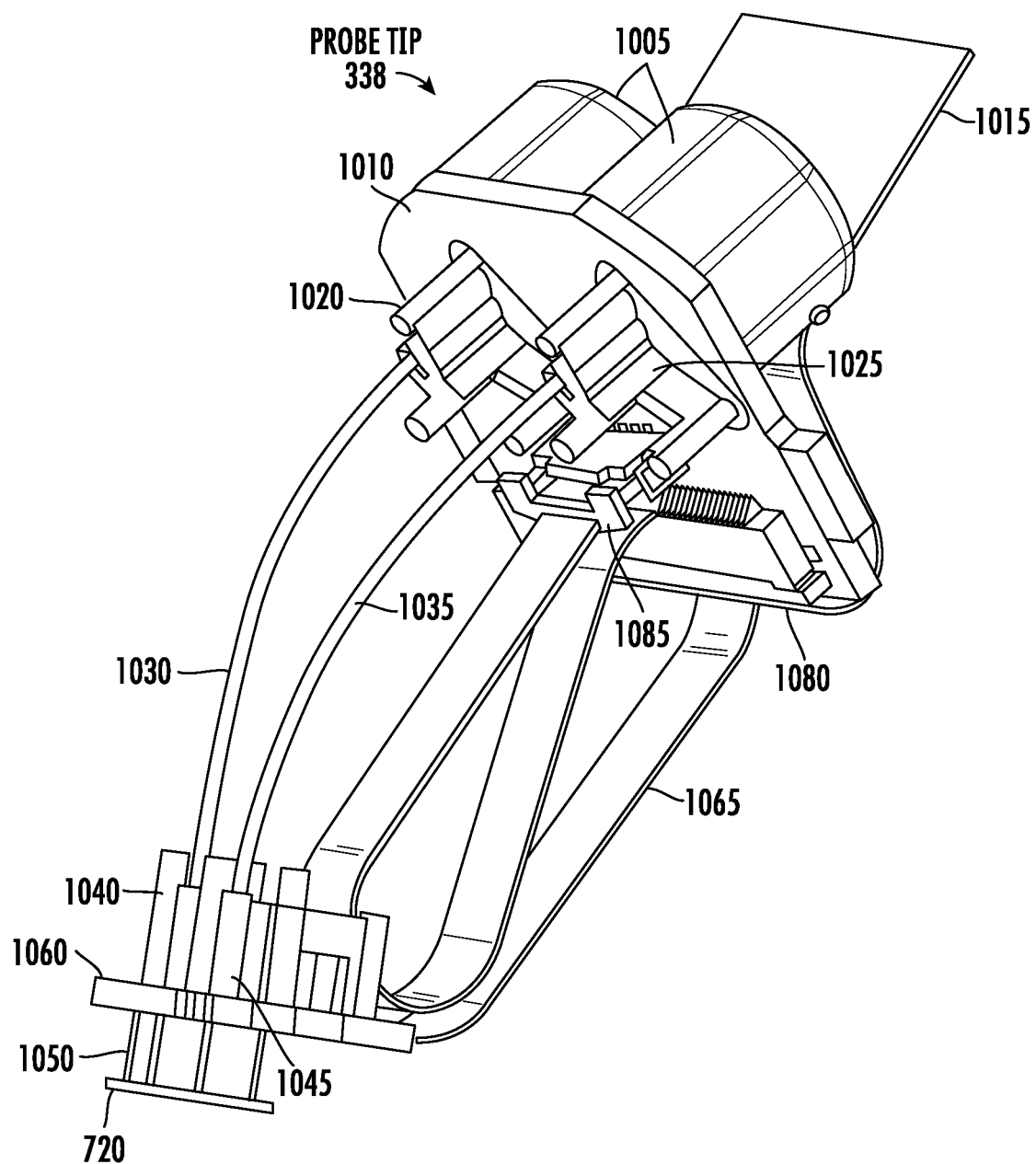
FIG. 11 shows the probe tip separate from the housing of the system unit and shows additional elements of the probe tip.

FIG. 11 shows the probe tip separate from the housing of the system unit and shows additional elements of the probe tip. As shown in this figure, the probe tip additionally includes an aperture plate 720, a first electrical connector 1080, and a second electrical connector 1085.

Figure 12:
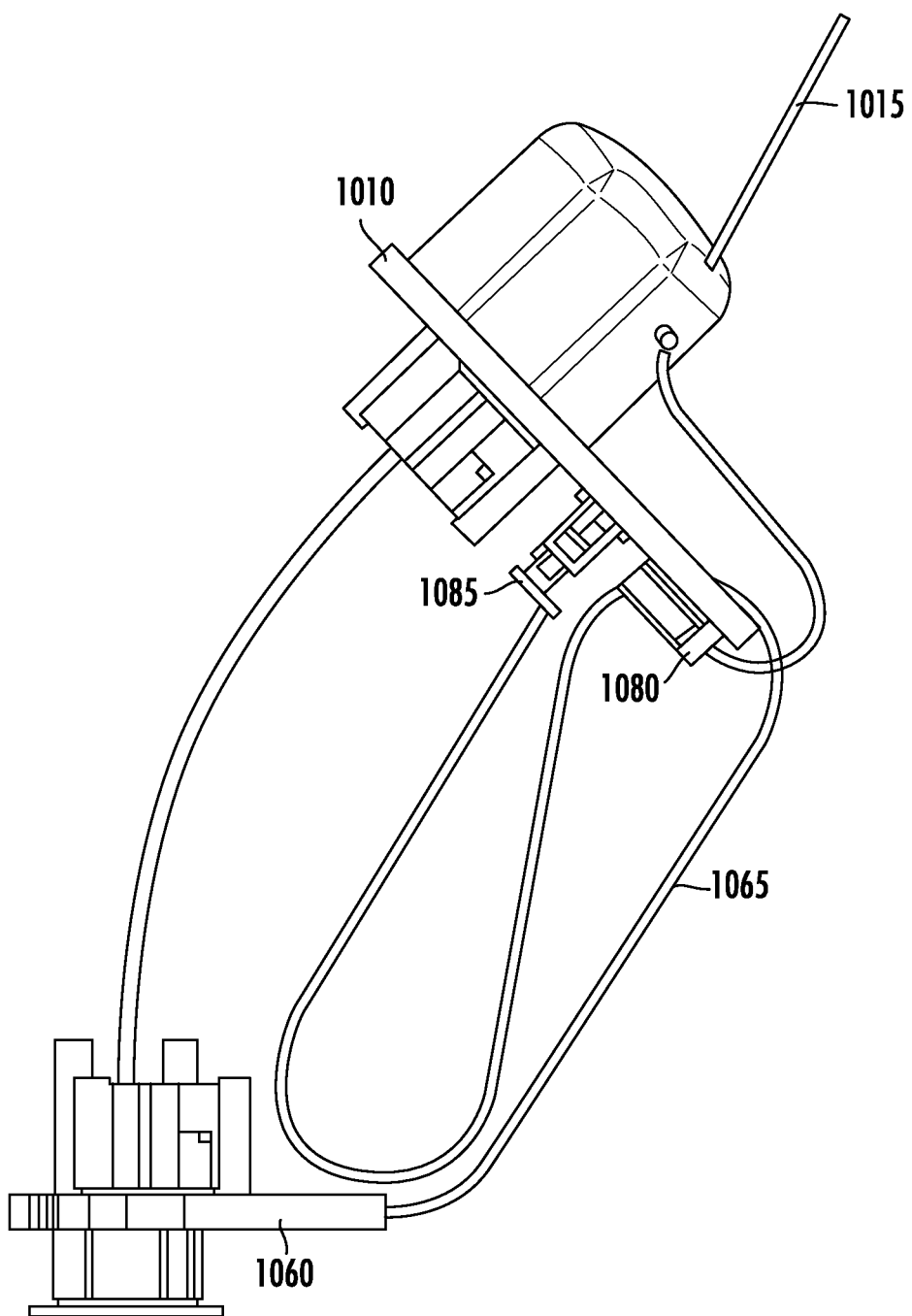
FIG. 12 shows a side view of the probe tip.

FIG. 12 shows a side view of the probe tip. A first end of ribbon cable 1065 is connected to second electrical connector 1085, which is mounted on LED PCB 1010. A second end of ribbon cable 1065 is connected to second PCB 1060. A first end of ribbon cable 1015 is connected to first electrical connector 1080, which is mounted on the LED PCB. A second end of ribbon cable 1015 is connected to the processor PCB 1093, such as via an electrical connector similar to connector 1080.

The first ribbon cable transmits control signals from the processor to the LEDs mounted on the LED PCB so that the LEDs emit the described wavelengths. The second ribbon cable can transmit control signals from the processor to the photodetectors and can receive detection signals from the photodetectors. The received detection signals can be digitized signals that are digitized by an A-to-D converter that may be mounted on the processor PCB. The received signal may also be preprocessed by a DSP connected between the A-to-D converter and the processor. The first and second ribbon cable can be flexible printed cables (FPCs) or other types of ribbon cables. Connectors for connecting the ribbon cables to the PCBs can be flat flex connectors (FFCs) or other types of connectors.

In an implementation, the angle between the surfaces (shown in a side-on view in FIG. 12) of PCBs 1010 and 1060 is from about 65 degrees to about 75 degrees. In another implementation, the angle between PCBs 1010 and 1060 is from about 66 degrees to about 68 degrees. In another implementation, the angle between PCBs 1010 and 1060 is from about 67 degrees to about 68 degrees. In another implementation, the angle between PCBs 1010 and 1060 is from about 66 degrees to about 67 degrees. The angle between the PCBs allows for the optical fibers of the probe tip to be curved and have a longer length than if the optical fibers were straight. The longer length of the curved optical fibers allows light travelling through the optical fibers to have a longer path which facilitates a uniform distribution of the light when the light reaches the ends of the optical fibers at the probe face of the probe tip. Uniform light at the ends of the fibers facilitates relatively uniform light irradiation on tissue that oximetry measurements are made for. The uniform irradiation facilitates predictable irradiation distribution on the tissue and thus allows for relatively accurate oximetry measurements made by the oximeter device.

In an implementation, first end portions of optical fibers 1030 and 135 that are held by the first optical fiber holder 1020 and second optical fiber holder 1025 are approximately perpendicular to the surfaces of PCB 1010. Second end portions of optical fibers 1030 and 135 that are held by the third optical fiber holder 1040 and fourth optical fiber holder 1045 are approximately perpendicular to the surfaces of PCB 1050 and to the surfaces of the aperture place of the probe tip. The perpendicular orientation of the fibers to the surfaces of the PCBs allows for the ends of the optical fibers that collect light from the LEDs and that emit light into tissue in a predictable manner. For example, the optical fibers will emit light in a direction that is perpendicular to the probe face of the probe tip and perpendicular to a surface of tissue being measured. The known transmission angle of the light from the probe face allows for reliable transmission angle into the tissue and reliable oximetry measurements with a relatively high quality value.

In an implementation, the angle between the surface (shown in a side view in FIG. 12) of PCBs 1010 and 1050 is from about 65 degrees to about 75 degrees. In another implementation, the angle between PCBs 1010 and 1050 is from about 66 degrees to about 68 degrees. In another implementation, the angle between PCBs 1010 and 1050 is from about 67 degrees to about 68 degrees. In another implementation, the angle between PCBs 1010 and 1060 is from about 66 degrees to about 67 degrees.

Figure 13:
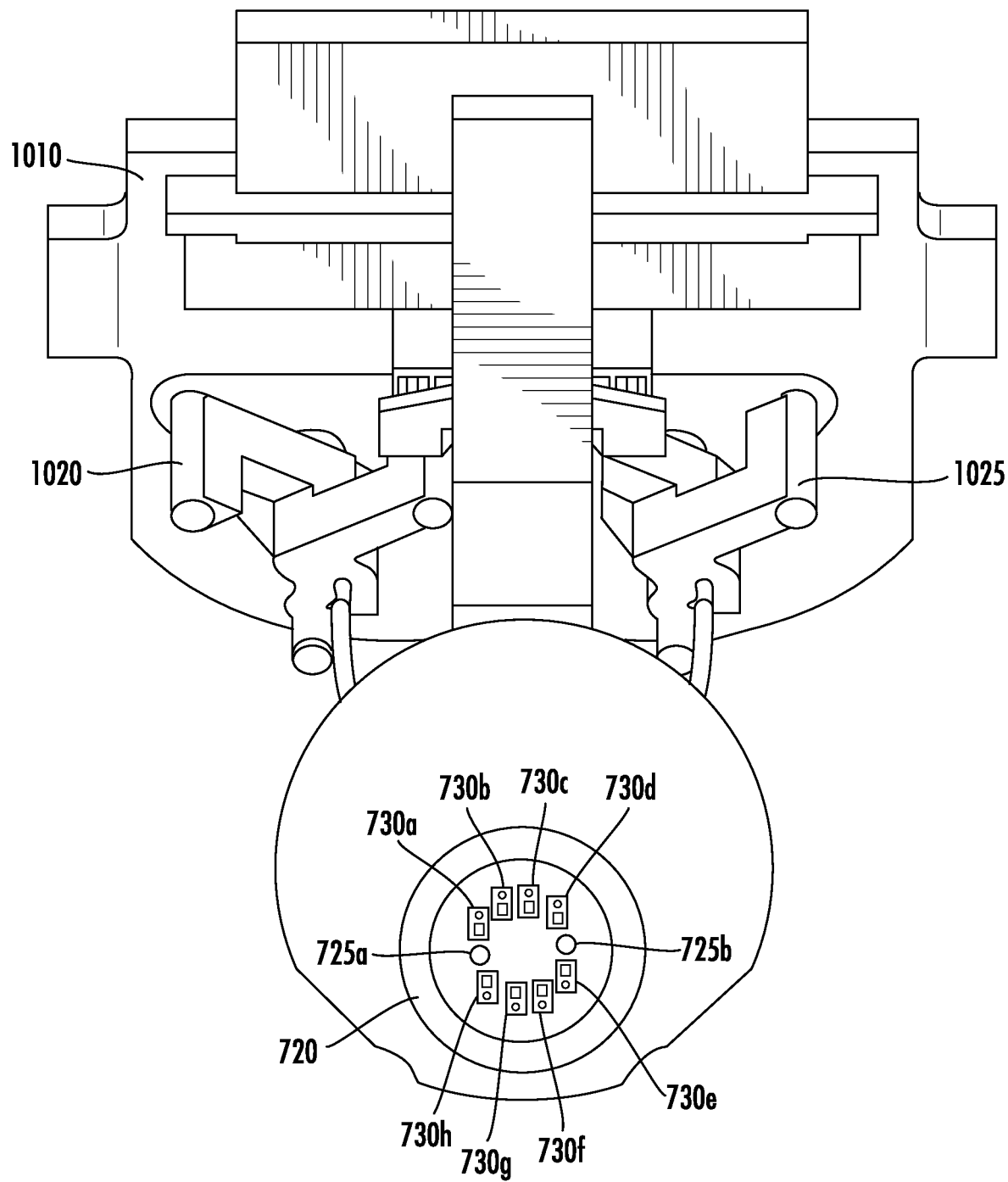
FIG. 13 shows an end view of the aperture plate.

FIG. 13 shows an end view of the aperture plate 720. This figure shows the source apertures 725a and 725b and shows the detector apertures 730a-730h.

Referring to FIGS. 10-13, the first and second optical fiber holders are connected to a second side of the LED PCB. The first and second optical fiber holders respectively hold first ends of the first and second optical fibers. The third and fourth optical fiber holders are connected to a first side of the second PCB 1060. The third and fourth optical fiber holders respectively hold second ends of the first and second optical fibers.

The first PCB 1050 and the second PCB 1060 are connected. A first side of the first PCB is connected to a second side of the second PCB. The first and second PCBs can be attached via an adhesive (epoxy) or via mechanical fasteners, such as screws.

The first and second PCBs may each include apertures (two apertures) for the optical fibers (e.g., two optical fibers). End portions of the optical fibers may be located in the apertures and held in place by the third and fourth optical fiber holders that are mounted to the first side of the second PCB. The photodetectors are mounted on a second side of the first PCB. The aperture plate includes an aperture (e.g., ten apertures in total) for each photodetector (e.g., eight photodetectors) and for the optical fibers (e.g., two optical fibers). The end portions of the optical fibers can be located respectively in two of the apertures in the aperture plate.

Figure 14:
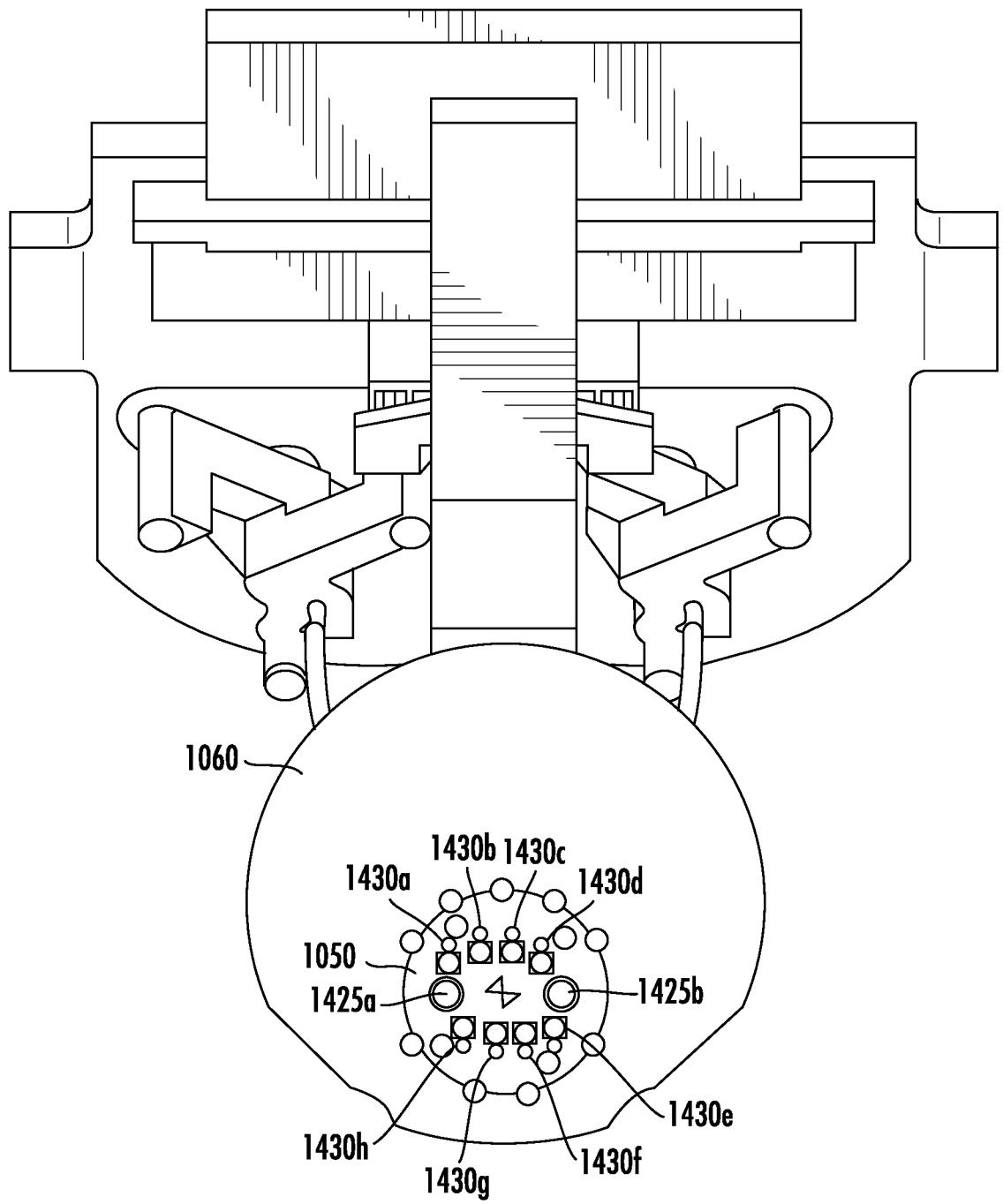
FIG. 14 shows the first PCB of the probe tip.

FIG. 14 shows the first PCB 1050. The first PCB includes source apertures 1425a and 1425b through which the first and second optical fiber may extend. Detectors 1430a-1430h are mounted on the first PCB. Electrical trances of the first PCB 1050 are connected to electrical traces of the second PCB 1060.

Figure 15:
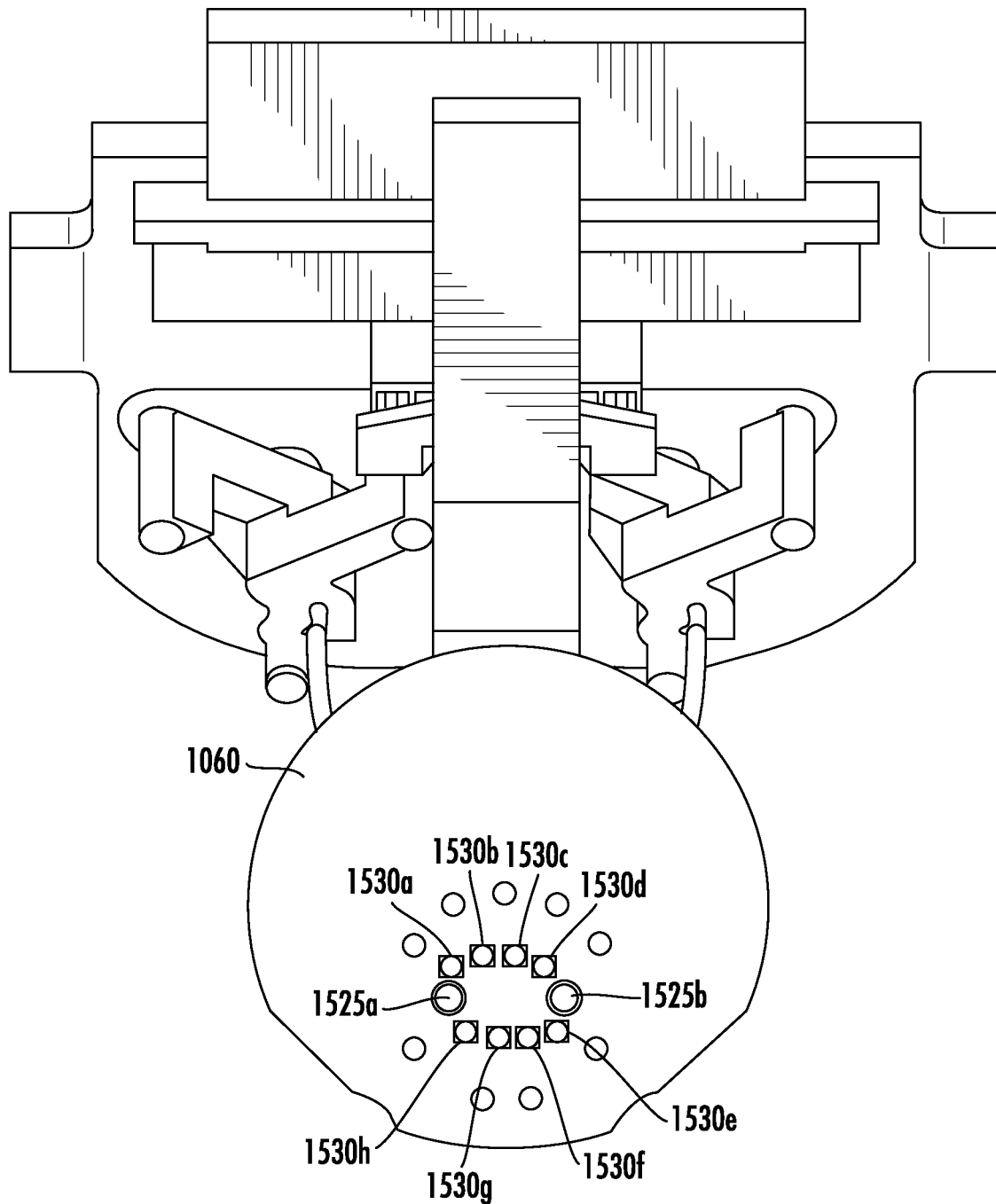
FIG. 15 shows the second PCB of the probe tip.

FIG. 15 shows the second PCB 1060. The second PCB includes apertures 1525a and 1525b through which the first and second optical fiber may extend. Electrical connector pads and electrical traces 1530a-1530h are formed on the second PCB and may connect to corresponding electrical connector pads and electrical trances of the first PCB 1050.

Figure 16:
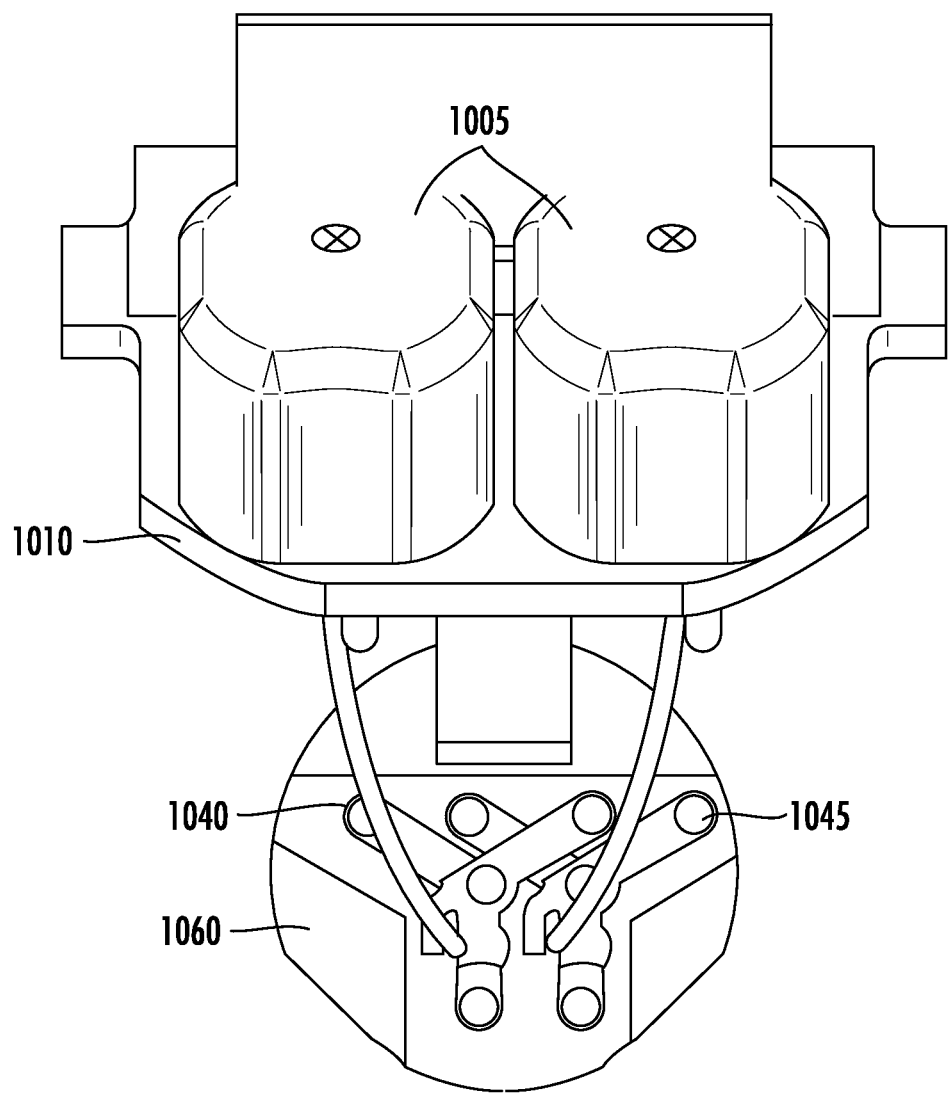
FIG. 16 shows a back view of the probe tip.

FIG. 16 shows a back view of the probe tip. This figure shows the two reflector domes 1005 mounted on the LED PCB 1010. Each reflector dome can direct light received from one or more LEDs into one of the optical fibers.

Figure 17:
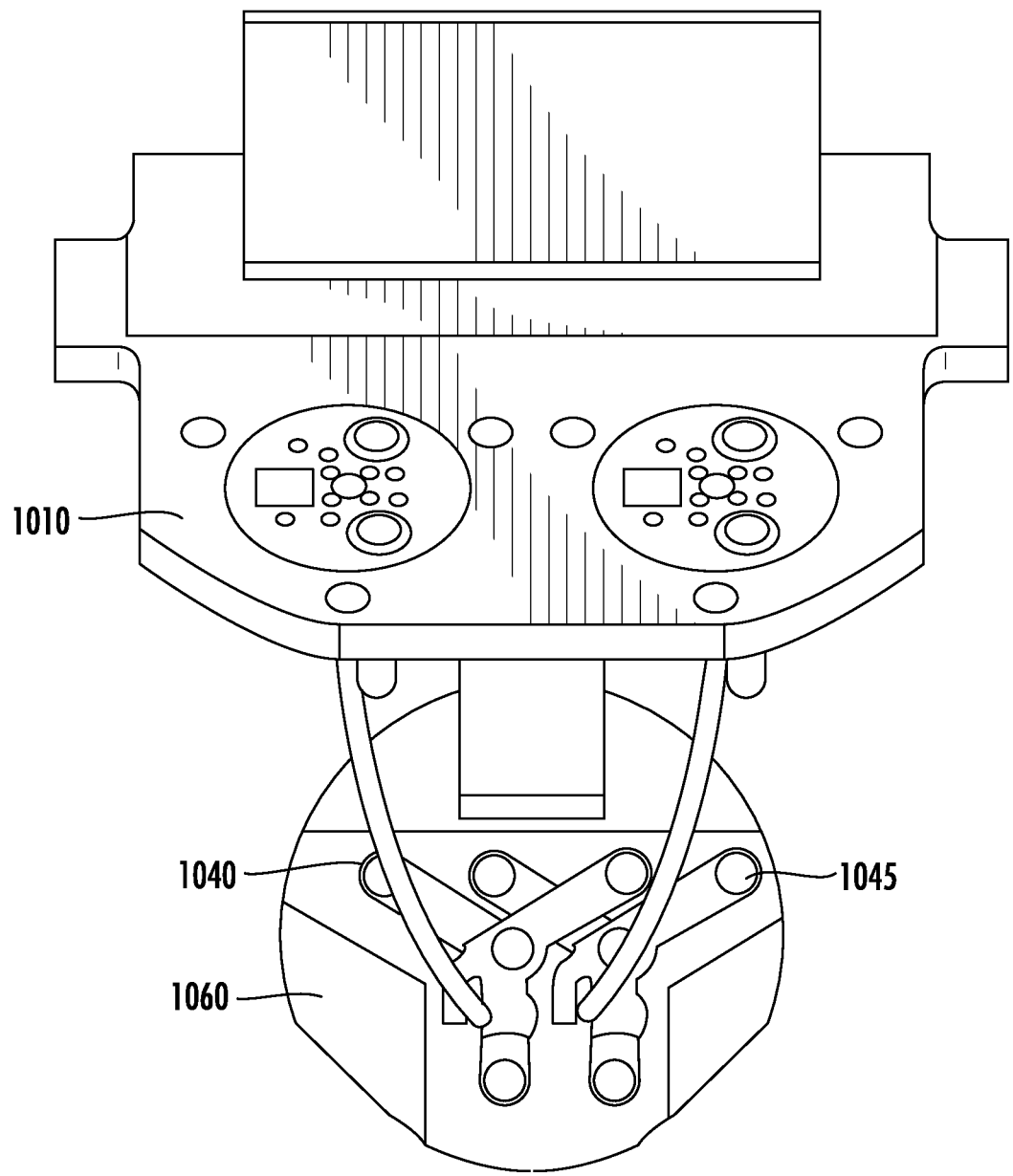
FIG. 17 shows a top view of the LED PCB of the probe tip.

FIG. 17 shows a top view of the LED PCB 1010. One or more LEDs (e.g., four LEDs) can be mounted on the LED PCB under each reflector dome. The LED PCB can include one or more aperture that portions of the optical fibers holder can extend into for adhesion of the optical fiber holder to the LED PBC.

Figure 18A:
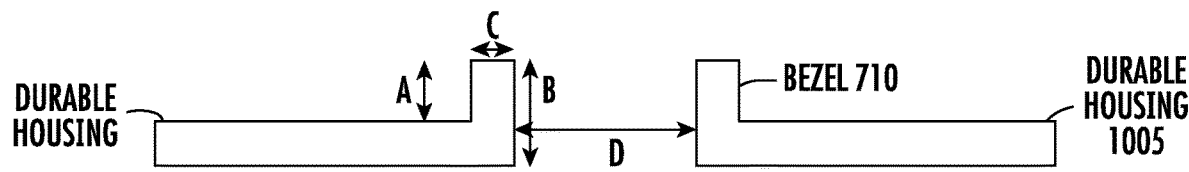
FIGS. 18A-18D show a number of steps for forming the probe face of the probe tip and forming the finished bezel of the housing of the system unit.

FIGS. 18A-18D show a number of steps for forming the probe face 715 of the probe tip 338 and forming the finished bezel 710 of the housing 1005 of the system unit 301. FIG. 18a shows the bezel 710 of the housing 1005 at an initial height A where the height is from the outside surface of the housing to the top of the bezel. Height A may be from about 3.5 millimeters to about 4 millimeters. In a specific implementation, height A is about 3.75 millimeters. The inner height B of the bezel is from the inside surface of the housing to the top of the bezel. Height B may be from about 4.5 millimeters to about 5.5 millimeters. In a specific implementation, height B is about 5.05 millimeters. The diameter D of the opening of the bezel may be from about 8 millimeters to about 10 millimeters. In a specific implementation, the diameter of the opening of the bezel may be about 9.1 millimeters. The width C of the bezel at the bezel's end may be about 1.0 millimeters to about 2.0 millimeters. The width C may vary around the circumference of the bezel. In a specific implementation, the width C of the bezel is about 1.5 millimeters.

Figure 18B:
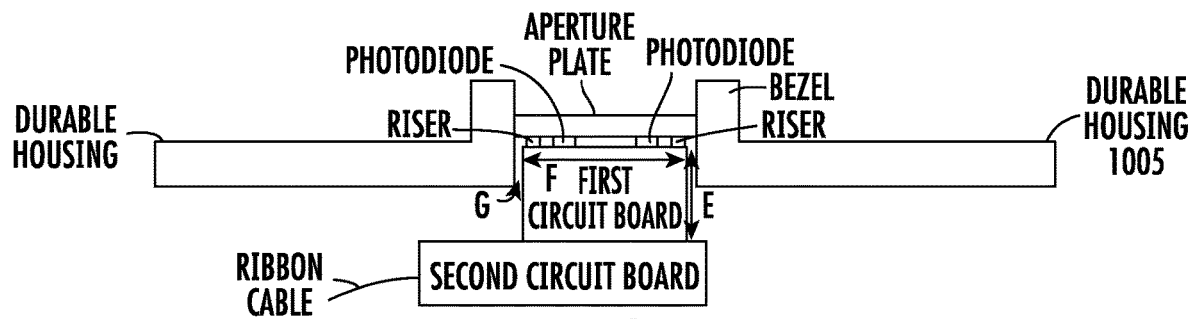

FIG. 18B shows the housing and bezel with a portion of the probe tip 338 in the housing and bezel. The portion of the probe tip shown includes a first circuit board 1020, a second circuit board 1025, riser 1030, photodiodes 1035, an aperture plate 1040, and a ribbon cable 1045 connected to the second circuit board. The first and second circuit boards may include electrical traces that are coupled. The second circuit board may be a fiberglass circuit board (e.g., FR4) that includes electrical traces that are connected to electrical traces of the first circuit board. The electrical traces of the first circuit board may extend upward from the second circuit board along the outer surface of the first circuit board. The first and second circuit boards may be connected by mechanical fasters, plastic welding, an adhesive (e.g., epoxy), another material, or any combination of these materials. The first circuit board may have a diameter F of about 6 millimeters to about 8 millimeters. In a specific implementation, the diameter F of the first circuit board is about 7 millimeters. The first circuit board may have a height E of about 3 millimeters to about 4 millimeters. In a specific implementation, the height E of the first circuit board is about 3.5 millimeters.

A distance G between the side of the first circuit board and the inner sidewall of the bezel may be about 0.5 millimeters to about 1.5 millimeters. In a specific embodiment, the distance between the side of the first circuit board and the inner sidewall of the bezel may be about 1.05 millimeters.

The riser may be connected to both the first circuit board and the aperture plate and may separate the first circuit board and aperture plate may be predetermined height. The photodiodes may be mounted on a top surface of the first circuit board and be connected to the electrical traces of the first circuit board. The aperture plate may include an aperture for each photodiode that is mounted on the first surface of the first circuit board and the diodes may respectively be inside the apertures. The height of each riser may be about 100 micrometers to about 200 micrometers. In an implementation, the height of each riser is about 150 micrometers.

Figure 18C:
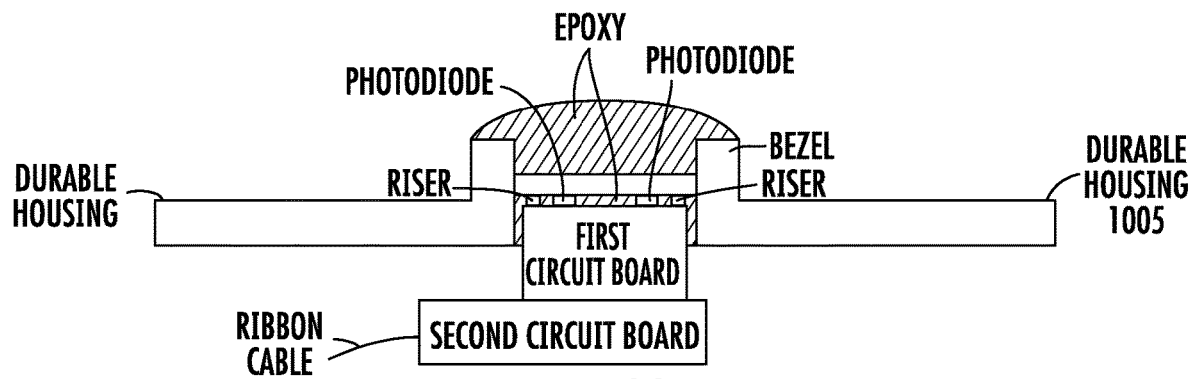

After the portion of the probe tip shown in FIG. 18B is placed into the opening of the bezel, epoxy is flowed into the opening as shown in FIG. 18C. The epoxy may flow into the apertures of the aperture plate, along the sides of the first circuit board, and may flow to the second circuit board and around the sides of the second circuit board.

Figure 18D:
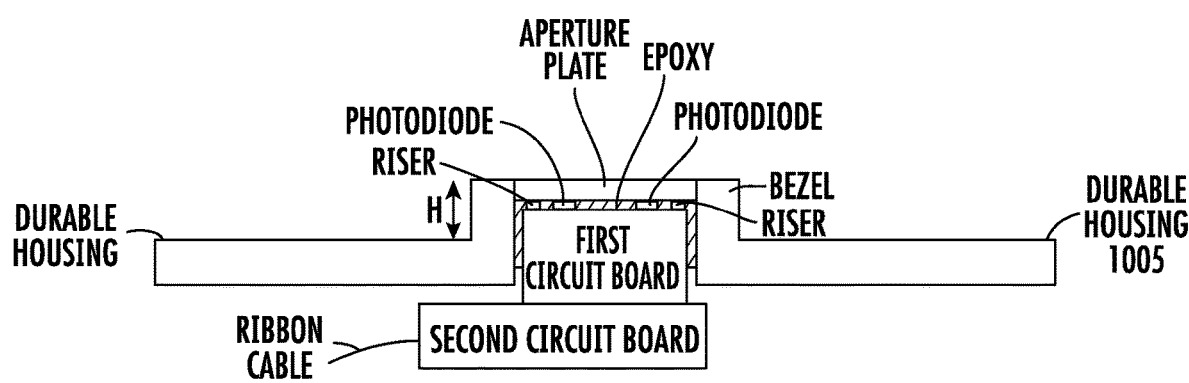

After the epoxy cures, the epoxy and a portion of the side of the bezel may be removed (e.g., polished down) to a final height, as shown in FIG. 18D. The final outside height H of the bezel may be about 2.0 millimeters to about 3 millimeters. In a specific implementation, the final outside height H of the bezel is about 2.58 millimeters. In an implementation, a portion of the aperture plate may also be thinned (e.g., polished thinner) when the bezel and epoxy are removed. The aperture place may be thinned to a final thickness from about 0.01 millimeters to about 0.03 millimeters (e.g., about 0.02 millimeters). A tolerance for the thickness of the aperture plate after polishing is from about + or −50 micrometers to about + or −60 micrometers (e.g., + or −56 micrometers). The aperture plate can include a marker embedded in the plate at about the center of the plate between the front and back surfaces. The embedded marker is exposed and polished away in the polishing process, the polishing is completed when the marker is polished away. Epoxy remains in the apertures formed in the aperture plate when the embedded marker is polished away. Further, there is epoxy over the top surfaces of the photodetectors after the polishing is completed. The thickness of the epoxy over the photodetector is about 350 micrometers to about 450 micrometers (e.g., about 400 micrometers).

In an implementation, the epoxy is polished down to the surface of the tops of the photodetectors inside the apertures of the aperture plate. In another implementation, a thin layer of epoxy remains over the tops of the photodiodes after polishing. In another implementation, a thin layer of epoxy remains over the tops of the photodetectors after polishing. In another implementation, a thin layer of the tops of the photodetectors is removed from polishing. In an implementation, a layer of epoxy is over the bezel sidewall and the front surface of the aperture plate. The layer of epoxy may be from about 5 micrometers to about 50 micrometers. In an implementation where the top surface of the aperture plate is in the sidewall of the durable housing after polishing, a layer of epoxy is in the opening in the sidewall and over the front surface of the aperture plate that faces outward from the sidewall. The layer of epoxy may be from about 5 micrometers to about 50 micrometers.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
providing a housing;
providing a probe tip, housed by housing at a distal end of the housing and visible from the exterior of the housing at the distal end of the housing, wherein the probe tip is coupled to a processor; and
providing that the probe tip comprises a first printed circuit board (PCB), a second PCB, and a first optical fiber coupled to the first and second PCBs, the first PCB is positioned closer to a proximal end of the housing than the second PCB, the second PCB is positioned closer to the distal end of the housing than the first PCB, a first surface of the first PCB faces the distal end of the housing, a second surface of the second PCB faces the proximal end of the housing, an angle between the first and second surfaces is nonzero, a first end portion of the first optical fiber located at the first PCB is approximately transverse to the first surface of the first PCB, a second end portion of the first optical fiber located at the second PCB is approximately transverse to the second surface of the second PCB, and a portion of the first optical fiber between the first and second end portions of the first optical fiber is curved.

2. The method of claim 1 comprising providing a first fiber coupler coupled to the first surface of the first PCB, wherein a first fiber aperture is formed in the first fiber coupler, the first end portion of the first optical fiber is positioned in the first fiber aperture, and the first fiber coupler holds the first end portion of the first optical fiber transverse to the first surface of the first PCB.

3. The method of claim 2 wherein the first fiber coupler holds a first end surface of the first end portion of the first optical fiber parallel to the first surface of the first PCB.

4. The method of claim 2 comprising providing a second fiber coupler coupled to the second surface of the second PCB, wherein a second fiber aperture is formed in the second fiber coupler, the second end portion of the first optical fiber is positioned in the second fiber aperture, and the second fiber coupler holds the second end portion of the first optical fiber transverse to the second surface of the second PCB.

5. The method of claim 4 wherein the second fiber coupler holds a second end surface of the second end portion of the first optical fiber parallel to the second surface of the second PCB.

6. A device comprising:
a housing; and
a probe tip, housed by the housing distal to a proximal end at a distal end of the housing and visible from the exterior of the housing at the distal end of the housing, wherein the probe tip is coupled to a processor,
the probe tip comprises a first printed circuit board (PCB), a second PCB, and a first optical fiber coupled to the first and second PCBs, the first PCB is positioned closer to the proximal end of the housing than the second PCB, the second PCB is positioned closer to the distal end of the housing than the first PCB, a first surface of the first PCB faces the distal end of the housing, a second surface of the second PCB faces the proximal end of the housing, an angle between the first and second surfaces is nonzero, a first end portion of the first optical fiber located at the first PCB is approximately transverse to the first surface of the first PCB, a second end portion of the first optical fiber located at the second PCB is approximately transverse to the second surface of the second PCB, and a portion of the first optical fiber between the first and second end portions of the first optical fiber is curved.

7. The device of claim 6 comprising a first fiber coupler coupled to the first surface of the first PCB, wherein a first fiber aperture is formed in the first fiber coupler, the first end portion of the first optical fiber is positioned in the first fiber aperture, and the first fiber coupler holds the first end portion of the first optical fiber transverse to the first surface of the first PCB.

8. The device of claim 7 wherein the first fiber coupler holds a first end surface of the first end portion of the first optical fiber parallel to the first surface of the first PCB.

9. The device of claim 7 comprising a second fiber coupler coupled to the second surface of the second PCB, wherein a second fiber aperture is formed in the second fiber coupler, the second end portion of the first optical fiber is positioned in the second fiber aperture, and the second fiber coupler holds the second end portion of the first optical fiber transverse to the second surface of the second PCB.

10. The device of claim 9 wherein the second fiber coupler holds a second end surface of the second end portion of the first optical fiber parallel to the second surface of the second PCB.

11. The device of claim 9 wherein the housing comprises a bezel located at the distal end of the housing, wherein the probe tip comprises an aperture plate located in the bezel, the aperture plate comprises a third fiber aperture, and the second fiber coupler orients the fiber parallel to the third fiber aperture in the aperture plate.

12. The device of claim 6 wherein the angle between the first and second surfaces is less than ninety degrees.

13. The device of claim 12 wherein the angle between the first and second surfaces is from about 65 degrees to about 70 degrees.

14. The device of claim 6 comprising a first ribbon cable that couples the first PCB to the processor.

15. The device of claim 14 comprising a second ribbon cable that coupled the second PCB to the processor through the first PCB.

16. The device of claim 15 wherein the probe tip comprises a light emitting diode (LED) coupled to a second surface of the first PCB; and a light directing element that optically coupled the LED to the first optical fiber, wherein the first and second surface of the first PCB are opposite surfaces of the first PCB.

17. The device of claim 6 wherein the probe tip comprises a second optical fiber coupled to the first and second PCBs, a first end portion of the second optical fiber located at the first PCB is approximately transverse to the first surface of the first PCB, a second end portion of the second optical fiber located at the second PCB is approximately transverse to the second surface of the second PCB, and a portion of the second optical fiber between the first and second end portions of the second optical fiber is curved.

* * * * *